United States Patent [19]
Fiorini et al.

[11] Patent Number: 5,125,731
[45] Date of Patent: Jun. 30, 1992

[54] MECHANICAL DEVICE FOR POSITIONING THE HEAD OF A PATIENT IN PERIMETER DEVICE

[75] Inventors: Fausto Fiorini, Monteguerrano Sutri(VT); Renzo Mattioli, Rome; Giuseppe Trombetti, Cisterna di Latina, all of Italy

[73] Assignee: Optikon Oftalmologia S.p.A., Roma, Italy

[21] Appl. No.: 557,571

[22] Filed: Jun. 24, 1990

[30] Foreign Application Priority Data

Jul. 31, 1989 [IT] Italy ................. 48258 A/89

[51] Int. Cl.⁵ .................. A61B 3/10; A61B 3/00
[52] U.S. Cl. .................. 351/245; 351/212; 351/247
[58] Field of Search ............ 351/214, 212, 245, 247; 128/633, 745; 606/4, 5, 6

[56] References Cited

U.S. PATENT DOCUMENTS 4,128,317 12/1978 LeCover .................. 351/214 X

Primary Examiner—Rodney B. Bovernick
Attorney, Agent, or Firm—Trexler, Bushnell, Giangiorgi & Blackstone, Ltd.

[57] ABSTRACT

A mechanical device for positioning the head of a patient in electromedical apparatuses, which device comprises a chin-rest and a headrest element held by two vertical rods, in which device mechanical means for bringing the same to a position displace of about 15° to the right or to the left with respect to the center of the hemispherical dome of the electromedical apparatus, means for fastening the position of the patient's head, means that allow said fastening means to be adjusted and fastened by acting on one or on the other indifferently of said rods and mechanical means for adjusting the vertical position of the chin-rest are provided.

6 Claims, 4 Drawing Sheets

MECHANICAL DEVICE FOR POSITIONING THE HEAD OF A PATIENT IN PERIMETER DEVICE

The present invention relates to a mechanical device for positioning the head of a patient in electromedical apparatuses.

More particularly, the present invention relates to a device of said type, particularly, though not exclusively, suitable for instruments for measuring the visibility threshold, that allows an optimum and constant patient head's positioning to be achieved.

BACKGROUND OF THE INVENTION

It's well known that in several instruments commonly employed in ophthalmology it is very important that a patient holds his/her head in a predetermined position, that is symmetrical for the right and for the left eye.

This need is particularly felt in the instruments for measuring the vision threshold, such as optical field meters and perimeters.

A perimeter is an instrument consisting of a hemispherical dome onto which light spots are projected of intensities and sizes determined at will by the examining operator.

A patient, sitting in front of the dome, lays his/her head on an adjustable device, commonly referred to as chin-rest, and fixes his/her selected eye, while the other is blindfolded, on a spot at the center of the dome. The patient must press a button as soon as he/she sees the luminous stimulus projected onto the dome.

The interpolation of all the peripheral spots seen gives a map that defines the visual field.

The operator must be sure that the patient doesn't lose his/her staring during the test. Such a check is performed by means of a telescope or of a telecamera arranged behind a hole at the center of the hemispherical dome.

In the more sophisticated instruments an optoelectronic system is provided, which automatically senses the losses of staring, following which the projection being performed is unvalidated or momentarily suspended.

Obviously, these systems, being based on the detection of the movements of the eye's image taken by the telescope or by the telecamera, are more sensitive to the lateral movements of the head than to the rotation of the eye with respect to the point fixed with the eye.

That makes it even more important that the chin-rest keeps the patient's head still as much as possible.

To this end, a belt which arrests the head has been adopted in some chin-rests.

Such a solution is increasingly discarded as it causes a considerable feeling of constraint to the patient.

Moreover, in the apparatuses used at the present day, the point to be fixed with the eye coincides with the hole at the center of the hemispherical dome, so the visual range cannot be examined correspondingly to this hole as it is not possible to project luminous spots there.

In addition, by constantly staring at a black hole on a white surface, an effect is created by which a retina area much greater than that of the hole itself is sensitized, whereby the test turns out to be not very reliable correspondingly to this area.

That involves, in addition, a disagreeable effect, whereby the patient's difficulty to keep his/her head firm for a long time increases.

SUMMARY OF THE INVENTION

The Applicant, being well aware of the problems mentioned above, and of the specific requirements in this field, has realized a mechanical device for positioning the head of a patient, or chin-rest, which device is able to obviate these and other drawbacks allowing the head to be so positioned, as to shift the point stared of through 15° toward the right or toward the left with respect to the center of the hemispherical dome, such that the central hole falls into the blind spot, that is to say, the area of the visual range that has a null physiological sensitivity, corresponding to the attachment of the optical nerve to retina.

The device according to the present invention is so structured as to cause the head to rotate through 15°, and not only the stared point, in such a way as to prevent the nose from covering a portion of the visual range.

Another object of the present invention is to provide a chin-rest which is endowed with adjustable matching elements for fixing the head, without having to make use of chains or the like, so avoiding a constraint feeling for the patient.

These and other objects are achieved according to the present invention by suggesting to realize a device for positioning the head of a patient in electromedical apparatuses, in which device a system for positioning the head of the patient in such a way as to shift the point stared by the right eye or by the left eye through 15° with respect to the center of the hemispherical dome, and a system for stopping the position of the head which is automatically adjustable by acting upon one only of the support rods of the head-rest are provided.

It is therefore a specific object of the present invention a mechanical device for positioning the head of a patient in electromedical apparatuses, which device comprises a chin-rest element and a head-rest element supported by two vertical rods, in which device mechanical means for positioning the same shifted to the right or to the left of about 15° with respect to the center of the hemispherical dome of the electromedical apparatus, means for fastening the position of the patient's head, means that allow said fastening means by acting indifferently upon one or upon the other of said rods to be adjusted, and mechanical means for adjusting the vertical position of the chin-rest element are provided.

In particular, said mechanical means for positioning the device according to the present invention with an orientation of about 15° to the right or to the left with respect to the center of the hemispherical dome, are made up of a horizontal bracket, in which said rods and the support of the chin-rest are coupled, endowed with two guide pins slidable in two shaped slots, symmetrical with respect to the chin-rest, realized on a fixed guide, the motion of said bracket being achieved by mechanical driving means.

Said mechanical driving means may be made up of slide means, coupled to said bracket, and slidable on rails under the drag of an worm screw coupled to a motor through a joint.

In addition, two optical stops may be provided for locating the motion of the slide means and an optical stop, arranged on the slide means themseleves, to detect if the device is positioned for the right eye or for the left eye.

Again according to the present invention, said means for fastening the position of the head are made up of two matching elements of a soft material which the two rods are endowed with.

The means which allow the fastening means to be adjusted and fixed are preferably made up of two handles, which the said rods are respectively endowed with, for moving the rods themselves, of two pins, arranged at the bottom of each rod, each inserted in a slot realized on a template arranged above the said bracket that makes the two rods substantially integral to each other in their rotation around the vertical axis, and of means for fastening the position, the head-rest element being hinged on the two rods in such a way, as not to undercome the same rotations.

Further, according to the present invention, said mechanical means for vertically adjusting the position of the chin-rest element may be made up of a guide pin, on which the chin-rest has been fixed, fastened to a screw means that drag slide means and coupled to first gear means moved by second gear means connected, in turn, to a motor.

Said slide means may be endowed with four wheels, that stabilize their position.

Moreover, two further optical stops may be provided.

BRIEF DESCRIPTION OF THE DRAWINGS

The present invention will be now disclosed according to its preferred embodiments, with particular reference to the figures of the annexed drawings, in which.

DESCRIPTION OF THE PREFERRED EMBODIMENTS

Figure 1:
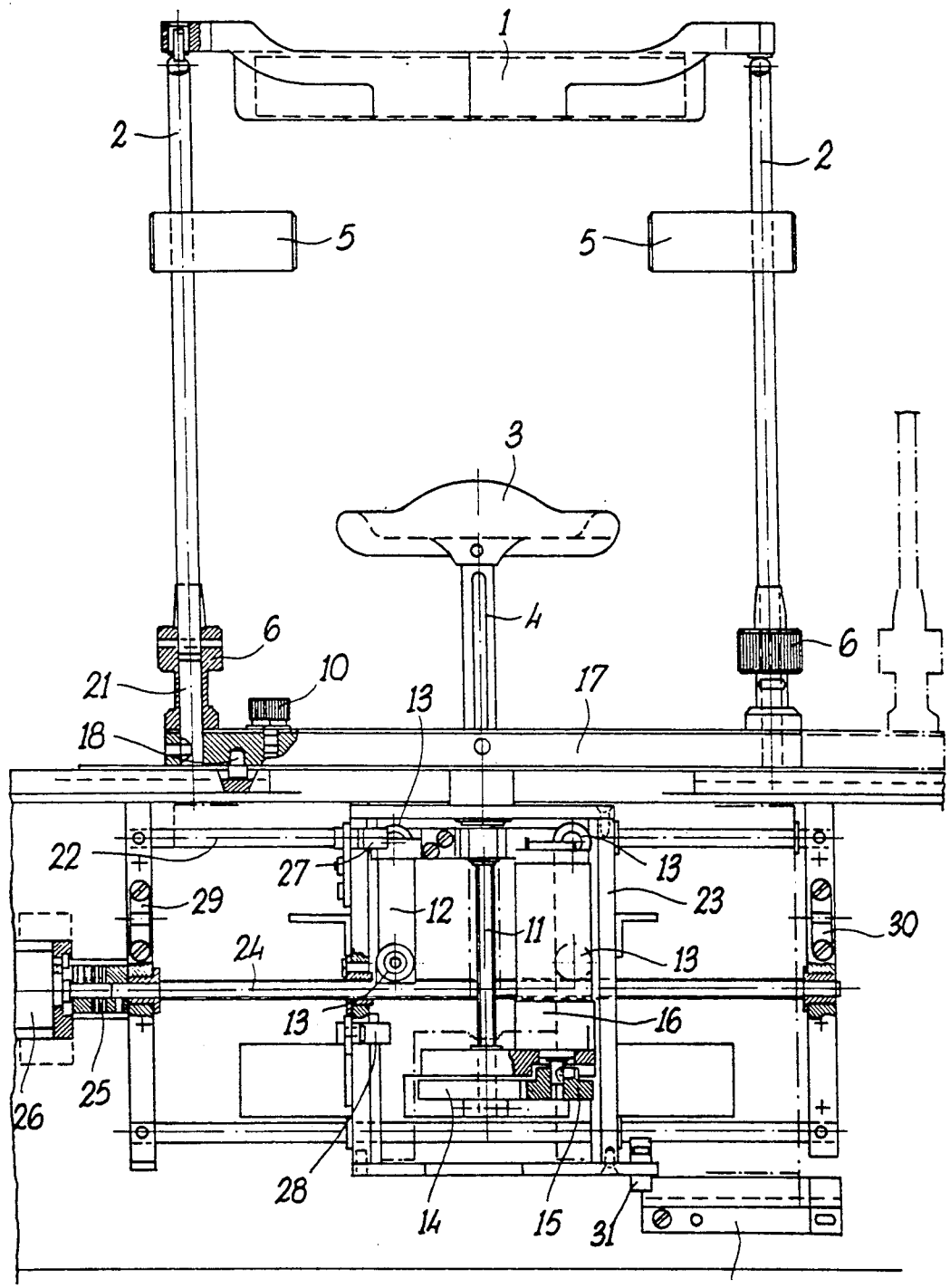
FIG. 1 is a rear view of the fastening device according to the present invention.

With reference to all the figures of the annexed drawings, and particularly to FIG. 1, the device according to the present invention, which is endowed with a forehead-rest 1, pivoted on the rods 2, and with a chin-rest 3, positioned on the guide-pin 4, is illustrated.

Two matching elements 5 are arranged on the two rods 2 in order to fasten the head of the patient.

Figure 3:
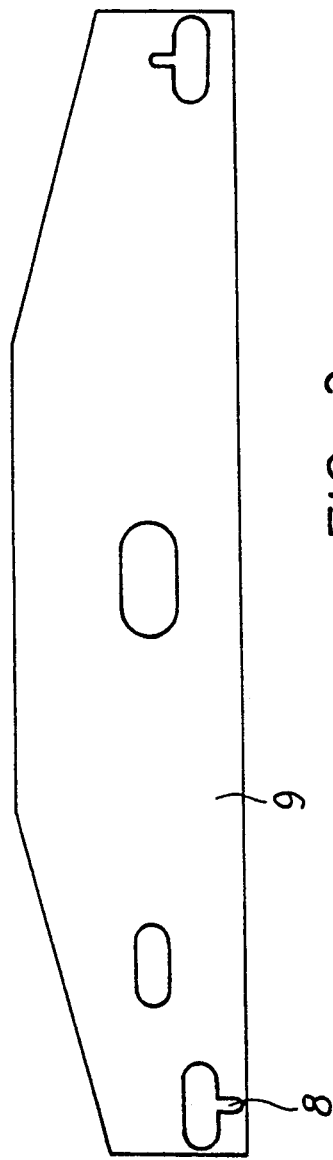
FIG. 3 is a top view of a second detail of the device of FIG. 1.
Figure 4:
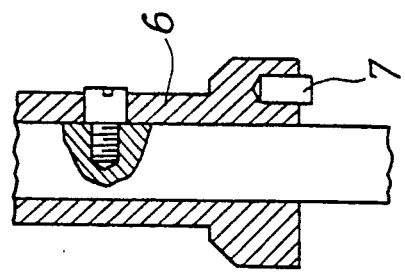
FIG. 4 is a view, in a vertical section, of a third detail of the device of FIG. 1.

At the bottom, the two rods 2 are endowed with handles 6, each provided with a pin 7 (see FIG. 4). One inserts said pins 7 in the slots 8 of the template 9 (see FIG. 3). In this way, by rotating one only of the handles 6, the corresponding pin 7 drags the template 9 determining the motion of the other rod 2 also.

Therefore, by acting on one only of the two handles 6, the rotation of either rods is determined and, consequently, the fastening of the head by virtue of the matching elements 5.

The position of this structure is fixed, once the desired arrangement has been achieved, by means of the fixing knob 10.

The guide-pin 4 of the chin-rest 3 is coupled to a screw 11 that in turn drags a slide 12 which brings, at its extremities, four nylon wheels 13 which stabilize its motion.

The screw 11 is fixed to a gearwheel 14 moved by a pinion 15 connected to the motor 16 that determines the vertical movements.

Figure 2:
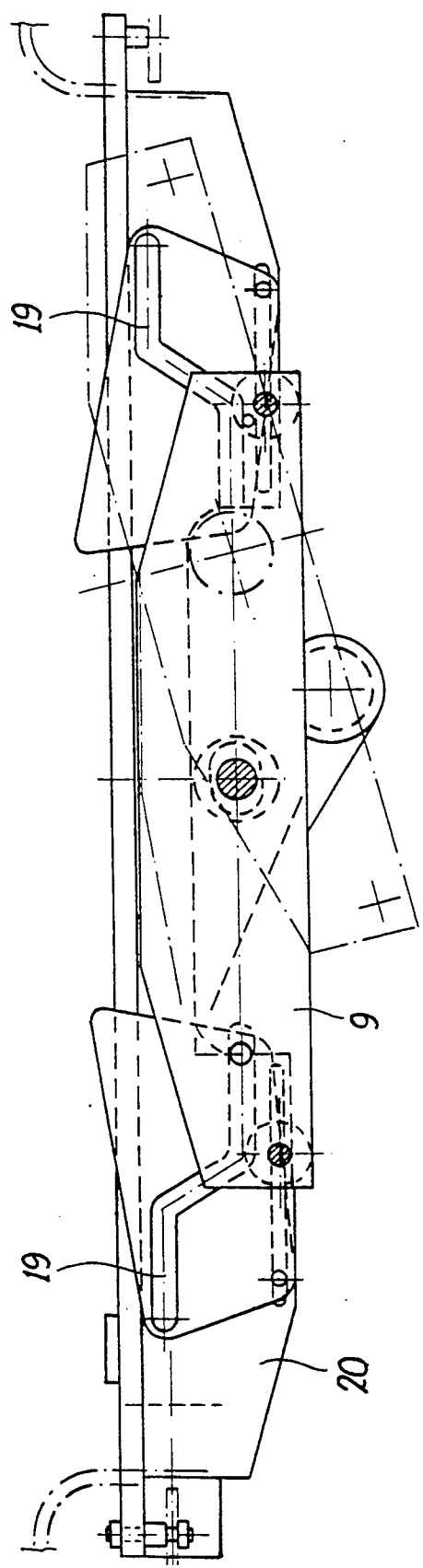
FIG. 2 is a top view of a first detail of the device of FIG. 1.

A bracket 17 on which two guide pins 18 slidable at the interior of two shaped slots 19, realized on the guide 20 (see FIG. 2), are mounted, is provided to displace the device according to the present invention through 15° to the right or to the left.

The two lower pins 21 of the rods 2 are fixed on said bracket 17.

The bracket 17 slides on the rails 22 integrally with the slide 23, dragged by the worm screw 24. Said worm screw 24 is connected to the motor 26 by means of an elastic joint 25.

The device according to the present invention is also endowed with four optical switches 27, 28, 29 and 30 that control the vertical stop (27 and 28) and the horizontal stop (29 and 30).

A fifth optical switch 31, assembled on the slide 23, detects if the device according to the present invention is positioned for the right eye or for the left eye.

When the slide 23 and the switch 31 are displaced to the right, the switch cooperates with the fixed platelet 32 that determines its closing or its opening.

The structure of the device is such that the component parts aren't obstacles in the visual range and that do not obstruct the light spots projected into the perimeter.

Figure 5:
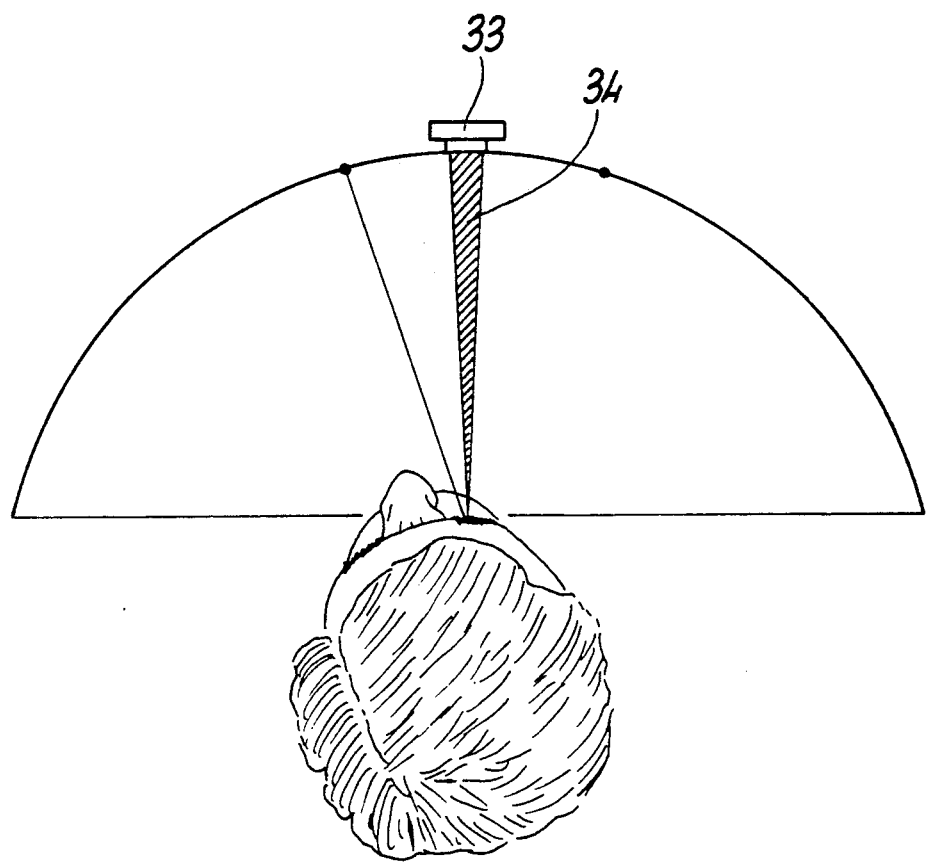
FIG. 5 shows schematically the fastening that is obtained with the device according to the present invention.

In FIG. 5 one can see, in a plan view, how the head is positioned with a device according to the present invention.

With the reference number 33 the telecamera is pointed out by which the operator checks the position of the head of the patient.

The point stared at by the (right or left) eye is displaced of 15° with respect to the hole of the telecamera, so that the area 34 of the blind spot turns out to be coincident with the axis of said hole.

It is advisable that the device according to the present invention gives the head a rotation slightly greater than the 15° mentioned above, being set forth that the stared point must be displaced of 15° with respect to the central hole, in order to avoid the shadow of the nose.

The present invention has been described with specific reference to some of its preferred embodiments, but it is to be understood that variations and/or changes may be made by those who are skilled in the art, without so departing from the scope of the enclosed claims.

We claim:

1. A mechanical device for positioning the head of a patient in an optical field perimeter, said perimeter comprising a hemispherical dome, which device comprises a chin-rest element, a head-rest element supported by two vertical rods and means for fastening the position of the head of the patient, characterized in that the device further comprises mechanical means for positioning the device itself in a position that is displaced of about 15° to the right or to the left with respect to the centre of said hemispherical dome, and in that said fastening means are made up of two handles provided respectively on said rods, for displacing the rods themselves; of two pins provided at the bottom of each rod, each inserted in a slot realized on a template arranged above the said bracket which makes the two rods substantially integral to each other in their rotation around the vertical axis; and of means for fastening the position; the head-rest element being pivoted on the two rods, so as not to undercome the same rotation.

2. A device according to claim 1, characterized in that said mechanical means for the vertical adjustment of the position of the chin-rest element are made up of a guide pin, on which the chin-rest element is fixed, said pin being fixed to screw means that drag slide means and are coupled to first gear means moved by second gear means connected in turn to a motor.

3. A device according to claim 2, in which said slide means is endowed with four wheels that stabilize its position.

4. A device according to claim 2 or 3, in which two further optical stops are provided.

5. A mechanical device for positioning the head of a patient in an optical field perimeter, said perimeter comprising a hemispherical dome, which device comprises a chin-rest element, a head-rest element supported by two vertical rods and means for fastening the position of the head of the patient, characterized in that the device further comprises mechanical means for positioning the device itself in a position that is displaced of about 15° to the right or to the left with respect to the centre of said hemispherical dome. and in that said fastening means are made up of two handles provided respectively on said rods, for displacing the rods themselves; of two pins provided at the bottom of each rod, each inserted in a slot realized on a template arranged above the said bracket which makes the two rods substantially integral to each other in their rotation around the vertical axis; and of means for fastening the position; the head-rest element being pivoted on the two rods, so as not to undercome the same rotations, made up of a horizontal bracket, upon which said rods are laterally coupled, which bracket is provided with two guide-pins slidable in two shaped slots symmetrical with respect to the chin-rest, said slots being realized on a fixed guide; the motion of said bracket being obtained by slide means, coupled to said bracket, and slidable on rails dragged by a worm screw coupled to a motor by means of a joint.

6. A device according to claim 5, in which two optical stops for determining the motion of the slide means and an optical stop, arranged on the slide means themselves, for detecting whether the device is positioned for the right or for the left eye, are provided.

* * * * *